(12) United States Patent
Howard

(10) Patent No.: US 9,067,879 B2
(45) Date of Patent: Jun. 30, 2015

(54) PROCESS FOR MAKING RENEWABLE SOURCE-BASED CITRATE ESTERS AND ACYLATED CITRATE ESTERS

(75) Inventor: Stephen Howard, Sherman, IL (US)

(73) Assignee: Archer Daniels Midland Company, Decatur, IL (US)

( * ) Notice: Subject to any disclaimer, the term of this patent is extended or adjusted under 35 U.S.C. 154(b) by 322 days.

(21) Appl. No.: 13/816,275

(22) PCT Filed: Jul. 21, 2011

(86) PCT No.: PCT/US2011/044851
§ 371 (c)(1),
(2), (4) Date: Mar. 6, 2013

(87) PCT Pub. No.: WO2012/027038
PCT Pub. Date: Mar. 1, 2012

(65) Prior Publication Data
US 2013/0274389 A1    Oct. 17, 2013

Related U.S. Application Data

(60) Provisional application No. 61/376,288, filed on Aug. 24, 2010.

(51) Int. Cl.
| | |
|---|---|
| *C07C 69/704* | (2006.01) |
| *C07C 67/313* | (2006.01) |
| *C07C 67/08* | (2006.01) |
| *C07C 67/14* | (2006.01) |
| *C07D 303/38* | (2006.01) |
| *C07D 301/02* | (2006.01) |

(52) U.S. Cl.
CPC ............... *C07C 67/313* (2013.01); *C07C 67/08* (2013.01); *C07C 67/14* (2013.01); *C07D 303/38* (2013.01); *C07D 301/02* (2013.01)

(58) Field of Classification Search
CPC ...................................................... C07C 67/08
See application file for complete search history.

(56) References Cited

U.S. PATENT DOCUMENTS

| | | | |
|---|---|---|---|
| 6,194,580 B1 * | 2/2001 | Greenwald et al. | 546/48 |
| 7,728,166 B2 * | 6/2010 | Finmans et al. | 560/180 |

* cited by examiner

*Primary Examiner* — Paul A Zucker
(74) *Attorney, Agent, or Firm* — William B. Miller

(57) ABSTRACT

Improved processes are described for making trialkyl esters and acylated trialkyl esters of carboxylic acids, as well as epoxidized trialkyl esters and acylated trialkyl carboxylate esters, such as are used in developing plasticized PVC compositions. In particular, processes are described for conducting the esterification and acylation steps involved in making the acylated trialkyl esters in a single vessel without an intermediate purification step, by means of a Lewis acid metal triflate catalyst.

6 Claims, No Drawings

PROCESS FOR MAKING RENEWABLE SOURCE-BASED CITRATE ESTERS AND ACYLATED CITRATE ESTERS

This application is a 35 U.S.C. §371 national phase entry of International Application No. PCT/U.S. Ser. No. 11/144,851, filed Jul. 21, 2011, which claims priority from U.S. Provisional Application Ser. No. 61/376,288, filed Aug. 24, 2010.

This invention relates to polyvinyl halide plasticizers which have been derived from renewable materials, to the methods by which such plasticizers are made and to the polyvinyl halide compositions incorporating these plasticizers.

Polyvinyl chloride (PVC), the most common vinyl halide polymer, finds commercial application in a rigid, substantially unplasticized form and in a plasticized PVC form. Rigid PVC, with which the present invention is not concerned, is used for pipework, ducts and the like in which high chemical resistance is needed but not flexibility or pliability. Plasticized PVC, on the other hand, finds application in films, sheeting, wire and cable coverings, moldings, conveyor belting, toys and hose, in addition to serving as a leather substitute and as a fabric covering for upholstered furniture, automotive seating and other articles. In these various end uses, both homopolymers and copolymers of vinyl chloride are found, so that henceforth "PVC" or "polyvinyl chloride" as used herein will be understood to cover the range of homo- and copolymer resins of vinyl chloride in which the citrate esters and acylated citrate esters made by the processes of the present invention may find use, especially as primary plasticizers. Similarly, "polyvinyl halide" will be understood as embracing both homo- and copolymer resins based on vinyl halides other than vinyl chloride. Exemplary copolymers of vinyl chloride include those containing up to about 20% of such monomers as vinyl acetate, propylene, ethylene, diethyl maleate, dimethyl fumarate, and other ethylenically unsaturated monomers).

Broadly speaking, plasticizers are materials which are combined with polymers such as polyvinyl chloride to impart flexibility, extensibility and workability or some combination of these attributes to the polymer, as needed for a particular end use. Frequently, a combination of primary and secondary plasticizers is used, with the secondary plasticizers not acting in and of themselves to impart the desired attributes to the PVC but serving to improve the effectiveness of the primary plasticizer(s) and optionally offer other characteristics to a PVC composition in which the materials are incorporated.

Historically, the majority of primary PVC plasticizers have been petroleum-derived phthalates and benzoate compounds, dioctyl phthalate and diisononyl phthalate being notable examples. However, such petroleum-derived plasticizers are frequently expensive to produce and use because of fluctuations in the pricing and availability of petroleum, and are increasingly likely to remain so as petroleum reserves are reduced and new supplies prove more costly and difficult to secure. Further, certain of the petroleum-derived phthalate plasticizers have raised concerns for their potential to disrupt human endocrine activity, and regulatory controls have been established in a number of countries to address these concerns. As well, a number of manufacturers of materials used for human contact, such as blood bank bags, intravenous tubing, kidney dialysis tubing and pacifiers, have voluntarily discontinued the use of phthalate plasticizers because of these health and safety concerns.

In view of the dependence of conventional primary PVC plasticizers on increasingly scarce and costly petroleum resources and especially in view of the concerns surrounding the phthalate plasticizers, renewable source-based primary plasticizer alternatives have been earnestly sought. It has been appreciated, for example, that some phthalates can be replaced by renewable source-based citrate esters, as described in greater detail below. Citric acid demand for plasticizer manufacture in 2009 in this regard amounted to about 2-3 thousand metric tons.

A number of citrate ester plasticizers, such as acetyl tributyl citrate, triethyl citrate, tributyl citrate, acetyl triethyl citrate and tri-2-ethylhexyl citrate, have been accepted by the United States Food and Drug Administration (USFDA) for use in plastic wraps that come into contact with food and have a long history of use in medical and pharmaceutical applications, as well as food and beverages. Citrate ester plasticizers can be used in vinyl resins and films, and some are also suitable for use in cellulose acetate and cellulose nitrate gums and resins. Citrate ester plasticizers have additionally been shown to be suitable plasticizers for use in acrylic, methacrylic, ethylcellulose, hydroxymethyl cellulose, nitro cellulose, vinyl acetate, vinyl chloride, vinylpyrrolidone, vinylidene chloride and urethane polymers.

More particularly, certain lower molecular weight citric acid alkyl esters, such as triethyl citrate and tributyl citrate, have a free hydroxyl group in the citrate backbone, and can replace low molecular weight phthalates, adipates, and sebacates in some polymers. Such lower molecular citric acid esters are suitable for use in human-contact applications (hair spray, deodorants, nail polish, and food contact). Certain higher molecular weight acylated citric acid alkyl esters have a carboxylic acid ester-bonded to the hydroxyl group of the citric acid backbone, and can replace phthalates (such as di-2-ethylhexyl-phthalate (DEHP)) and adipates (such as di-2-ethylhexyl adipates (DEHA)). These higher molecular citric acid esters are also suitable for use in human-contact applications (vinyl toys, vinyl gloves, nail polish, paper coating, foil coating, and food contact).

Synthesis of the acylated citrate esters, such as acetyl triethyl citrate and acetyl tri-n-butyl citrate, has been cumbersome. Both the carboxylic acid moieties and the hydroxyl moieties of citric acid must be esterified with co-reactant alcohols and co-reactant carboxylic acids, respectively, to form these materials. However, if the citric acid is mixed with both the co-reactant alcohols and co-reactant carboxylic acids at the same time, unwanted esters are formed between the co-reactant alcohols and co-reactant carboxylic acids, lowering yield and requiring extensive purification. Consequently, synthesis of the acylated citric acid esters has traditionally required two steps, with two different catalysts. Catalyst from the first reaction is often destroyed by neutralization before being removed from the product of the first step. In addition, achieving high yields in the second step has been difficult.

In a first aspect, the present invention concerns a novel process for the synthesis of trialkyl esters of carboxylic acids generally and of trialkyl citrate esters particularly, wherein the trialkyl esters are formed by a Lewis acid metal triflate-catalyzed condensation reaction of a carboxylic acid, a carboxylic acid anhydride or chloride with an alcohol or mixture of alcohols. The novel use of a Lewis acid metal triflate catalyst enables the trialkyl esters to be formed in high purity, with minimal formation of byproducts, and further permits a process whereby the catalyst may be simply and economically recovered for reuse, as through water extraction and subsequent water removal (though other catalyst recovery methods are contemplated and will be described below).

In a second aspect, the present invention concerns improved processes for making acylated trialkyl esters of carboxylic acids generally, and acylated trialkyl citrates especially, wherein the trialkyl esters of a carboxylic acid are first formed in the presence of a Lewis acid metal triflate catalyst as just described, and then these trialkyl esters are acylated through reaction with additional carboxylic acid, carboxylic acid anhydride or chloride in the presence of a suitable catalyst, preferably being the same, Lewis acid metal triflate catalyst. Especially, the present invention in this second aspect concerns improved processes for producing acylated trialkyl carboxylate esters (such as the acylated trialkyl citrates which have found use as renewable source-based alternative plasticizers) wherein a single catalyst and a single reaction vessel may be used for carrying out the synthesis of a trialkyl carboxylate ester from an alcohol and a carboxylic acid, carboxylic acid anhydride or chloride as well as the subsequent acylation of the trialkyl carboxylate ester. As before, the use of a Lewis acid, metal triflate catalyst in the context of a "single pot", two-step process enables products of high purity to be formed, with minimal formation of byproducts, as well as facilitates an economical recovery and reuse of the catalyst.

In one preferred embodiment according to the second, broad aspect, Applicants have developed a facile, single catalyst, two-step process for synthesizing acylated trialkyl carboxylate esters in high yields. In the first step, a carboxylic acid, carboxylic acid anhydride or chloride (or a combination thereof) is reacted with an alcohol or mixture of alcohols in the presence of a triflate catalyst. In the second step, the tertiary hydroxyl of the carboxylic acid is acetylated in the presence of the same catalyst. The entire process can be accomplished using a single reactor without purifying or isolating the product from step 1 or adding additional catalyst for step 2. Alternatively, of course, where the trialkylcarboxylate esters are the desired product, the esterification step can be carried out in the presence of the Lewis acid metal triflate catalyst. In either case, the catalyst is then preferably recovered as indicated above and recycled for reuse.

Various water-tolerant, Lewis acid metal triflate catalysts may be used, for example, bismuth and neodymium triflates, as well as lanthanide triflates. Very small amounts of catalyst are required, for example, as little catalyst as 0.05 percent by mass or even less based on the carboxylic acid, depending on the particular reactants and reaction conditions. These triflate catalysts can be employed as is and recovered by washing the crude product with water, followed by evaporating the water, as demonstrated by the examples below. The catalyst may also precipitate out and be recovered at least in part by filtration, or the triflate catalyst might be incorporated on or into a solid substrate and recovered again by filtering rather than extraction; those skilled in the art will be well able to determine an appropriate method by which the Lewis acid metal triflate catalyst can be present in the system and subsequently recovered on completion of the reaction(s) for reuse.

The process is preferably carried out under atmospheric pressure and at temperatures close to the reflux temperature of the alcohol or alcohol mixture. Under reflux conditions, azeotropic water is continually removed to drive the process to completion. Preferred alcohols are immiscible with water, have from four to eight carbons and especially are branched C4 to C8 alcohols, for example, isobutyl alcohol, isoamyl alcohol and 2-ethylhexyl alcohol, while the carboxylate moiety preferably is selected from the dicarboxylates, tricarboxylates and polycarboxylates and the anhydrides and chlorides of the associated carboxylic acids. Citric acid is a preferred carboxylic acid.

The trialkyl carboxylate esters and/or acylated trialkyl carboxylate esters may be used in a conventional manner as now realized for example with the known citrate ester plasticizers, to plasticize PVC and provide plasticized PVC compositions useful for making a variety of articles. The esters and acylated esters so formed may also be epoxidized, using any conventional method for accomplishing the epoxidation, and the epoxidized trialkyl carboxylate esters and epoxidized acylated trialkyl carboxylate esters used to form plasticized PVC compositions. Known epoxidation methods include exposure of the esters to strongly acidic media, for example, a peracid supplied from an external source or generated in situ from hydroperoxides and an organic acid in a strong mineral acid solution, or exposure to acidic solids in the presence of a catalyst. Exemplary epoxidation methods are further described in, for example, commonly-assigned United States Published Application No. 2009/0005508, U.S. Pat. No. 4,647,678, U.S. Pat. No. 6,740,763 and US Published Application No. 2008/0154053.

The plasticized polyvinyl halide compositions of the present invention can be formulated, it is noted, in all other respects in a conventional manner, including various kinds of additives in addition to the trialkyl carboxylate esters or acylated trialkyl carboxylate esters (or the epoxidized esters or acylated esters) as primary plasticizers. For example, a renewably-based secondary plasticizer and thermal stabilizer such as epoxidized soybean oil can be added, or other secondary plasticizers (including petroleum-based plasticizers) or other additives for improving one or more properties of heat stability, lubricity or weathering resistance, as ultraviolet absorbers, fillers, anti-oxidants, anti-static agents, anti-fogging agents, pigments, dyestuffs, crosslinking aids and the like can be incorporated in the compositions. The inventive epoxidized esters may also be blended with other primary plasticizers such as dioctylphthalate, other phthalates, citrates, benzoates, trimellitates, and other aliphatic diesters, though preferably the plasticized polyvinyl halide compositions of the present invention will not include any added phthalates and will include substantially only renewably-based or biobased plasticizers.

Applicants have in summary developed a process with significant advantages over known methods of synthesis of acylated trialkyl citrates: in a first step, rapid synthesis of trialkyl citrates takes place from citric acid and alcohol (typically and preferably over a period of less than three hours) using only a slight molar excess (about 0.3 molar excess, for example) of alcohol and using a very small amount of catalyst (0.05% or less, for example, as mentioned above); catalyst neutralization after the first step is obviated; purification of the trialkyl citrate after the first step is also obviated; a very small amount of catalyst (again, for example, 0.05% or less) is also used for the second step acylation of trialkyl citrate; the same catalyst is carried through both steps of the reaction; the second step is very rapid (typically and preferably requiring less than 15 minutes) using only a small amount (less than 0.2 molar excess, for example) of an acyl donor, such as acetic anhydride; active catalyst is recovered by simple water extraction after the second step; and the recovered catalyst retains its activity and can be used again. Those skilled in the art will appreciate that the process of the present invention provides like advantages and can be similarly described according to the first aspect of the present invention, wherein the second, acylation step is omitted and the desired trialkyl citrates are separated from the triflate catalyst through simple water extraction.

EXAMPLE 1

Acetylation of Triisobutyl Citrate

A trialkyl citrate (triisobutyl citrate, Fluka, St. Louis, Mo., 1 mL) was mixed with acetic anhydride (Aldrich, St. Louis, Mo., 1 mL), and a catalytic amount of neodymium III triflate (Aldrich, 0.025 grams) was added. The mixture in the vial was stirred at room temperature for 1 hour.

After one hour of reaction, the reaction mixture was analyzed by thin layer chromatography (TLC, 9:1 hexanes:ethyl acetate). The triisobutyl citrate had been consumed and a product had formed. The product co-spotted identically with a commercial sample of acetyl triisobutyl citrate. A second vial of reactants without catalyst was analyzed by TLC, and no reaction had taken place.

EXAMPLE 2

Benzoylation of Trialkyl Citrate

An alkylated citrate (triamyl citrate, Archer Daniels Midland, Decatur Ill., 400 grams) and benzoyl chloride (Aldrich, 160 mL, ~1.3 molar equivalents) were mixed under nitrogen and bismuth triflate catalyst (Aldrich, 0.700 grams) was added. The reaction mixture was heated to 60° C. for 6 hours under nitrogen. After six hours of reaction, a mixture of starting material and product was present. Additional bismuth triflate (0.500 grams) was added and the reaction mixture was stirred overnight at room temperature. After 16 hours of stirring the starting material was not detectable by TLC. The reaction mixture was washed with 250 mL of saturated sodium bicarbonate, which resulted in gas evolution and an emulsion. Methylene chloride (500 mL) was added to the emulsion and the emulsion broke after sitting overnight. The organic phase was removed and washed 3 times with 500 mL of deionized water and the organic phase was dried with anhydrous magnesium sulfate. Methylene chloride was removed under vacuum, resulting in a red oily product. The red product was diluted in hexanes (500 mL) and treated with 50 g activated charcoal by heating to 60° C. for 2 hours to decolorize the product. The solution was filtered over celite and the product condensed under vacuum to remove hexanes. The resulting oil was dried under vacuum overnight to yield 420 grams of an alkylated trialkyl citrate product (benzoyl triamyl citrate) having a molecular weight of 420 grams/mole and a Pt/Co color value of 427 (measured by ASTM method D1209). The product also had a low hydroxyl content (0.0108% OH value (average)) and a low acid value (2.0761), both indicating a high degree of esterification.

EXAMPLE 3

Pivaloylation of Trialkyl Citrate

Triamyl citrate (400 grams) and pivaloyl chloride (Aldrich, 175 mL, ~1.3 molar equivalents) were mixed under nitrogen and bismuth triflate catalyst (Aldrich, 0.700 grams) was added. The reaction was carried out for 16 hours substantially as described in Example 2, except the reaction was carried out at 60° C. without a second addition of catalyst. The product was washed and tested by TLC substantially as described in Example 2 except that the red product dissolved in hexanes was decolorized by refluxing with 30 grams of activated charcoal for three hours. The mixture was allowed to cool to room temperature and then filtered over a bed of celite. The solvent was removed under vacuum. The resulting oil was dried under vacuum overnight to yield 430 grams of a pivaloyl trialkyl citrate product having a molecular weight of 430 grams/mole, a Pt/Co color value of 72 (measured by ASTM method D1209), low hydroxyl content (0.0690% OH value (average)) and a low acid value (1.0948), indicating again a high degree of esterification.

EXAMPLE 4

Two Step Synthesis of Acetylated Trialkyl Citrates from Citric Acid

In a first step, an alcohol mixture having an estimated average molecular weight of 145 g/mole (CO-810™ light cut fatty alcohols (caprylic and decyl mix), CAS 68603-15-6, P&G Chemicals, Cincinnati, Ohio, 800 grams) and bismuth triflate (0.500 grams, Aldrich) were added to a 3 L roundbottomed flask fitted with Barratt style trap and reflux condenser. The mixture was stirred and citric acid (Archer Daniels Midland, Decatur Ill., 300 grams) was added as the reaction mixture was heated to reflux (between 110° C. and 135° C.). After 2 hours of reflux, 85 mL of water was collected in the Barratt trap. TLC analysis of the reaction mixture suggested that the formation of trialkyl citrates was complete. The reaction mixture was allowed to cool to room temperature and excess alcohol was removed under vacuum.

In the second step, the mixture of synthesized trialkyl citrate and bismuth triflate catalyst was brought to 30° C. and acetic anhydride (Aldrich, 175 ml (1.2 molar equivalents)) was added to the trialkyl citrate. The temperature of the reaction mixture rose to 60° C. immediately. After stirring the reaction mixture for 30 minutes, the completion of the synthesis of acetylated trialkyl citrate was confirmed by TLC. The liberated acetic acid and residual acetic anhydride were removed under vacuum. The resulting dark yellow product was diluted in hexanes and treated with activated charcoal (30 g), and the mixture was refluxed for 1.5 hours. The mixture was allowed to cool to room temperature and then filtered through a bed of celite. Hexanes were removed under vacuum and the resulting oil was dried under vacuum overnight to yield 560 grams of an acetyl trialkyl citrate product having a molecular weight of 560 grams/mole, a Pt/Co color value of 66 (measured by ASTM method D1209), very low hydroxyl content (0.0039% OH value (average)) and a very low acid value (0.0507), indicating substantially complete esterification.

EXAMPLE 5

Two Step Synthesis of Acetylated Trialkyl Citrate from Citric Acid with Recovery of Active Catalyst Isoamyl alcohol (Aldrich, 200 mL; 3.5 molar equivalents to citric acid) and bismuth triflate (0.200 grams) were placed in a 1 liter roundbottomed flask fitted with a condenser atop a Barrett trap and purged under nitrogen. Citric acid (Archer Daniels Midland, Decatur, Ill., 100 grams) was added to the flask and the reaction mixture was heated to reflux. As heating progressed, the citric acid dissolved. The reaction progress was monitored by the accumulation of water in the trap. After 2 hours, 27 mL of water had collected. The reaction mixture containing triisoamyl citrate was allowed to cool to room temperature. Excess isoamyl alcohol (~30 mL) was removed under vacuum and gentle heating.

The trialkyl citrate was allowed to cool to 35° C. and acetic anhydride (Aldrich, 60 ml, 1.2 molar equivalents) was carefully added. The temperature of the reaction mixture rose to 65° C. After 5 minutes, the triisoamyl citrate was almost completely acetylated as determined by TLC. The liberated acetic acid and residual acetic anhydride was removed under vacuum. The product was then washed with deionized water to partition the catalyst into the wash water phase. The washed product was diluted with hexanes and dried with magnesium sulfate (anhydrous). Hexanes were removed under vacuum and the resulting oil was dried under vacuum overnight to yield 192 grams of as acetyl trialkyl citrate product having a Pt/Co color value of 504.

Catalyst recovery from the wash water phase was carried out by water removal from the wash water phase, followed by dilution with hexanes and hexane removal under vacuum. An oily material (0.460 grams) was recovered.

The recovery of bismuth triflate catalyst in the recovered oily material was verified by reuse of the recovered oily material as a catalyst. Triisobutyl citrate (Fluka, 1 mL) was incubated with acetic anhydride (Aldrich, 0.5 ml, 1.85 molar equivalents) and the recovered oily material (10 mg) substantially as outlined in Example 3. After 1 hour, TLC analysis indicated the disappearance of triisobutyl citrate and the formation of acetyl triisobutyl citrate.

EXAMPLE 6

Acetylation of Triisobutyl Citrate and Triisoamyl Citrate

Two citrate polyesters substantially free from esters in their hydroxyl portion (triisobutyl citrate and triisoamyl citrate) were acetylated substantially as outlined in Examples 4 and 5 above to yield a mixture of acetylated triisobutyl citrate and acetylated triisoamyl citrate.

EXAMPLE 7

Acetylation of tri-(2-ethylhexyl)-citrate

Crystalline citric acid (ADM, 250 grams), 2-ethylhexanol (Aldrich, 650 mL), bismuth triflate (Aldrich, 250 mg) and toluene (200 mL) were stirred under nitrogen substantially as in Example 4 in a round-bottomed flask equipped with a Dean Stark trap. The temperature was raised to 130° C., and as the mixture refluxed the citric acid dissolved. After about 70 mL of water had been collected in the Dean Stark trap, the reaction mixture was allowed to cool to room temperature.

Acetic anhydride (Aldrich, 175 mL) was added to the cooled reaction mixture and an exotherm was observed that raised the temperature of the reaction mixture from about 20° C. to 35° C. About 30 minutes after addition of acetic anhydride, analysis by TLC indicated complete acylation of the tri-2-ethylhexyl citrate. The product was rotovapped to remove toluene, acetic acid and residual acetic anhydride, then washed with 1 liter of dilute sodium bicarbonate solution to remove residual acetic acid and bismuth triflate. The washed product was then washed twice with deionized water to obtain a viscous red-colored product. The viscous red-colored product was diluted with 500 mL hexane and then contacted with 30 grams of activated carbon to reduce color. After filtration to remove carbon and rotary evaporation to remove hexanes, a yellow oily product was obtained.

The organic layer was dried over magnesium sulfate, filtered, and rotovapped to remove hexanes, yielding the desired acetylated tri-(2-ethylhexyl)-citrate.

EXAMPLE 8

Acetylation of the Citrate of 10% Hexenol and 90% Ethylhexanol and Subsequent Epoxidization Crystalline citric acid was reacted with mixture of 10 wt % hexenol and 90 wt % 2-ethylhexanol, then acetic anhydride substantially as outlined in Example 7 to yield acetyl-(2-ethylhexyl/3-hexenyl (10%)) citrate.

The acetyl-(2-ethylhexyl/3-hexenyl (10%)) citrate was epoxidized as follows. In a procedure adapted from co-pending ADM patent application WO2006014483, a 3 gallon bucket was filled with ice and kept within reach during the epoxidation reaction. Hydrogen peroxide (50%, 219.14 grams, Sigma-Aldrich) and 96% formic acid (17.7 grams, Sigma-Aldrich) were chilled to between 0 and 10° C. Acetyl-(2-ethylhexyl/3-hexenyl (10%)) citrate (370.8 grams) mixed with water (74 mL) and Tween™ 20 nonionic polysorbate surfactant (1.78 grams, Sigma-Aldrich) in a 2 Liter jacketed round bottom flask with a bottom drain, an overhead stirrer, and an immersion thermocouple. A 4 Liter vessel filled with ice was positioned below the vessel, under the drain valve. The jacket temperature was set to 0° C. and the mixture of soy fatty acids benzyl esters, water, and Tween™ 20 were cooled to less than 10° C. The cold formic acid was carefully mixed with the hydrogen peroxide, taking care to make sure the mixture remained below 10° C.

The cold mixture of hydrogen peroxide and formic acid was carefully poured into the reaction flask, taking care to ensure that the temperature of the mixture remained below 10° C. The temperature was monitored via the immersion thermocouple. If the temperature began to climb rapidly, ice would be added directly to the reaction mixture. If added ice was insufficient to slow the temperature rise and it appeared that the reaction exotherm was out of control, the contents of the flask would have been drained through the drain valve onto the ice container below the vessel. The atmosphere in the flask was made inert with a slow nitrogen purge and the mixture was stirred at 300 rpm. After all of the cold mixture of hydrogen peroxide and formic acid was added (time zero), the temperature of the reaction mixture was 5.7° C. The temperature of the chiller was raised to 10° C., then raised by an additional 10° C. at 15 minutes, 30 minutes and 50 minutes. The temperature of the reactants as the reaction proceeded was 7.5° C. at 15 minutes, 14.8° C. at 30 minutes, and 26.4° C. at 50 minutes. The reaction was allowed to proceed for 20 hours.

After 20 hours, the contents of the flask were transferred to a 4 L separatory funnel and 350 mL of hexanes were added. The contents were mixed and allowed to separate. The aqueous layer was removed and the organic layer was washed twice with deionized water. After the second wash, the wash water reacted with peroxide indicator paper but turned purple, not black. The organic layer was washed with 350 ml of a solution of sodium bisulfite (1%) followed by washing twice with water (350 mL). After the second water wash the pH of the aqueous layer was about 2. The organic layer was washed with a 1% solution of sodium bicarbonate (350 mL), whereupon the pH of the aqueous layer was about 7. The sodium bicarbonate wash was removed and the hexanes layer was washed once with deionized water; the pH of the wash water after washing was about 5. The resulting material is referred to as epoxidized acetyl-(2-ethylhexyl/3-hexenyl (10%)) citrate, although only the hexenol had double bonds capable of being epoxidized.

After cooling under vacuum, the epoxidized acetyl-(2-ethylhexyl/3-hexenyl (10%)) citrate. had the properties indicated in Table 8-1.

TABLE 8-1

| Iodine value | Oxirane value | Hydroxyl value | Acid number | Color |
| --- | --- | --- | --- | --- |
| 6.19 | 0.99 | 0 | 4.16 | 262 |

The low iodine value indicates that few double bonds remained after epoxidation, and no free hydroxyl groups were detected.

Compounding, Evaluation Protocols for Examples 9 and Following:

Compounding of PVC Plastisols

The materials listed in Table A below were used for compounding a set of PVC plastisols. Control samples were formulated as reference samples using diisononyl phthalate (DINP), a commercial phthalate primary plasticizer, and experimental samples were formulated using acylated trialkyl citrates as primary plasticizers.

TABLE A

Raw Material List (Examples 9 and Following).

| Material | Brand Name | Generic Name | Source | Source Location |
|---|---|---|---|---|
| Geon 121AR | Geon ™ 121AR | Homopolymer PVC Dispersion Resin | PolyOne, Inc. | Avon Lake, OH |
| DINP | | Di-isononyl phthalate | | |
| ESO | Plas-Chek ™ | Epoxidized Soybean Oil | Ferro, Inc. | Cleveland, OH |
| Benzoyl Trialkyl Citrate | See Example 2 | | ADM | Decatur, IL |
| Pivaloyl Trialkyl Citrate | Example 3 | | ADM | Decatur, IL |
| Acetyl Trialkyl Citrate | Example 4 | | ADM | Decatur, IL |
| Acetylated triisobutyl citrate | Examples 6 and 7 | | ADM | Decatur, IL |
| Acetylated triisoamyl citrate | Example 6 | | ADM | Decatur, IL |
| Acetylated tri-2-ethyl hexyl citrate | Example 7 | | ADM | Decatur, IL |
| Epoxidized acetylated tri(hexenol/2-ethylhexyl) citrate | Example 8 | | ADM | Decatur, IL |
| LOHF 120 | Therm-Chek ™ | Ba/Zn stabilizer | Ferro, Inc. | Cleveland, OH |

Plastisol (PVC) Formulation Protocol

Materials from Table A were used in compounding plastisols in the following quantities: Geon 121AR Resin, 100 parts; plasticizer, 67 parts; epoxidized soybean oil, 3 parts; Ba/Zn stabilizer (LOHF 120), 2 parts. Weighed powdered solids were introduced to a 1-gallon mixing bowl. The primary plasticizer (DINP or one of acetyl trialkyl citrate, benzoyl trialkyl citrate, pivaloyl trialkyl citrate, triisobutyl citrate, acetylated triisobutyl citrate, triisoamyl citrate, acetylated triisoamyl citrate, or acetylated 2 ethylhexyl citrate) and other liquid components were combined in a separate container. The solids in the mixing bowl were stirred at the lowest speed of a 3-Speed Hobart Paddle Mixer, and the liquids were slowly added to the mixing bowl. The contents were mixed for about 30 minutes, and the mixture was subjected to vacuum (such as in a large dessicator) to reduce air entrapment.

Test Protocols for PVC Plastisol Examples

Where results are reported below for the various plastisol specimens (in Examples 9 and following), the corresponding tests were carried out according to the following protocols:

Paste Viscosity (Brookfield RV Viscosity)—

The paste viscosity of a plastisol specimen describes the flow behavior of plastisols under low shear. The suitability of a dispersion resin for a given application depends on the viscosity characteristics of the plastisol and indicates performance in pouring, casting, molding, and dipping processes. The Paste Viscosity Test (Brookfield Viscosity Test) was carried out substantially according to ASTM procedure D1824 using a Brookfield RVFD Viscometer. Measurements were made at room temperature at 2 revolutions per minute (RPM) and 20 RPM. Low initial paste viscosity is desired for ease of handling, with preferably as little increase as possible over time, so that the paste viscosity measurements were repeated on several occasions over 30 days to determine the stability of the paste viscosity of the plastisol specimens.

Gelation Temperature—

The gel curve and gelation temperature test is carried out to determine the viscosity of plastisols under increasing temperature with a CarriMed™ CSL-2 500 rheometer. The gelation temperature indicates the solvating power of the plasticizer; lower gelation temperatures indicate greater solvating power, and are preferred for convenience in applications such as screen printing, dip coating, and preparation of soft rubber compounds because less heat is needed to maintain low viscosity of the plastisols. The viscosity is plotted as a function of temperature, and analysis of the plot indicates an approximate gelation temperature. A 4 centimeter flat, steel spindle is attached to the rotor of the rheometer and the calibration routine is carried out to calibrate the spacing between the rheometer Peltier plate and the spindle. An increase in temperature from 20° C. to 100° C. (68° F. to 212° F.) at a rate of 0.1° C. (0.18° F.) per second with a constant shear rate of 5 sec-1 is programmed into the rheometer software. A 2 gram sample of plastisol is loaded onto the Peltier plate and the program is initiated. At the conclusion of the temperature ramp, the results are plotted as output of viscosity versus temperature on a semi-Log chart to produce a gel curve. Then, lines are hand-drawn asymptotically to the two sections of the gel curve, extending them toward the X axis until they intersect. The gel temperature is then approximated by noting the temperature corresponding to the intersection of the hand-drawn lines.

Air Release—

The Air Release Test is carried out to determine the relative speed of release of entrained air from a plastisol. Liquid plastisol is poured into at 4 ounce polypropylene cup or equivalent and the plastisol is stirred vigorously with a spatula for one minute. As the entrapped air rises to the surface, the rate at which the bubbles break is observed and recorded. A relative rating of "Excellent" to "Poor" is assigned by comparison with reference formulations. Excellent air release (5 minutes) is obtained with a reference formulation comprising 100 parts Geon™ 121AR, 67 parts DINP, 3 parts epoxidized soybean oil (ESO), and 2 parts Therm-Chek™ LOHF 120. Poor air release (>60 minutes) is obtained with a reference formulation comprising 100 parts Geon™ 121AR, 67 parts BBP, 3 parts ESO, and 2 parts Therm-Chek™ LOHF 120.

Hardness—

The Shore A Hardness test is carried out substantially according to ASTM D2240 using a Shore Durometer Gage to determine the hardness values of plastisols. Hardness is a measure of the efficiency of the plasticizer. At equal levels of incorporation of two different plasticizers in otherwise identical plastisols, the plasticizer yielding the softer plastisol is a more efficient plasticizer.

Heat Loss

The Heat Loss test is applied to fused plastisols to determine the percent loss of mass during heat aging. Low heat loss is desirable, as volatilized plasticizer can contaminate nearby surfaces, such as windshield interiors on new cars. Fused sheets of plastisol are prepared substantially as in the Heat Stability Test. Square samples (5.0 cm by 5.0 cm (2 inch by 2 inch)) are punched or cut and weighed to +/−0.0001 g. The samples are incubated in an 82° C. (180° F.) oven for 7 and/or 14 days, and cooled for 30 minutes before re-weighing. The heat loss is expressed as a percentage of the original weight of the sample.

Exudation Test—

Fused plastisol discs are made in aluminum weighing dishes using from 15+/−0.5 grams of liquid plastisol. Three discs per plastisol sample are prepared. The plastisols are fused for ten minutes in an oven preheated to 400° F. The discs are cooled quickly in water and removed from the aluminum dishes. To determine exudation, a stack of two fused plastisol discs is incubated in a 180° F. oven for at least 4 weeks. The discs are examined after 24 hours and weekly for at least four weeks and compared with an identical reference strip kept at room temperature. The visible presence of exudation is noted, and the amount exuded is determined by visual inspection. Exudation values are assigned as falling into one of the following ranges: none-trace-light-moderate-heavy.

Heat Stability—

The Metrastat Heat Stability test is used to measure the thermal stability of a plastisol film at high temperatures. Fused sheets of plastisols are prepared and exposed to high temperatures for varying time periods along the length of the strips. An excellent plastisol does not discolor or char and maintains flexibility after the test. Fused sheets of plastisol are prepared by "drawing down" plastisol onto a heat-stable surface (release substrate) using a 20 mil (0.020") drawing bar; the release substrate must be capable of withstanding at least 200° C. (390° F.) for 5 minutes. The fused sheets ("draw downs") are fused for 3 minutes in an oven at 200° C. (390° F.). Fused sheets are allowed to cool at room temperature for a minimum of 15 minutes before removing from the release substrate. Sample strips measuring 25 cm (9.75 inch) by 2.5 cm (1 inch) are cut from the fused sheets. A Metrastat™ oven is preheated to 191° C. (375° F.) and sample strips are placed onto the travelling tray of the Metrastat™ oven. A one hour exposure cycle is started. As the tray travels the sample strips are exposed to the oven temperature over a time gradient of 0-60 minutes. When the cycle is complete, sample strips are allowed to cool for 1 hour and mounted onto display paper which shows the time the sample was exposed to high heat.

Plasticizer Volatility—

The Plasticizer Volatility test (Raw Material Volatility) is used to determine the relative plasticizer volatility that may affect plastisol processing. Lower plasticizer volatility is desired, especially for compounded (extruded) plastisols. A 1-gram sample of plasticizer is accurately weighed (+/−0.0001 g) and incubated in an oven for 3 minutes at 204° C. (400° F.). The weight loss is determined and the percentage of weight loss is reported as plasticizer volatility.

EXAMPLES 9-11

Evaluation of Acylated Trialkyl Citrates as Plasticizers for PVC

The acylated trialkyl citrates synthesized according to the present invention in Examples 2-4 were incorporated into plastisols using ingredients listed in Table 9.1.

TABLE 9.1

Experimental Raw Material List

| Material | A | B | C | D |
|---|---|---|---|---|
| Geon 121AR Resin | 100 | 100 | 100 | 100 |
| DINP | 67 | 0 | 0 | 0 |
| Acetyl Trialkyl Citrate (Example 4) | 0 | 67 | 0 | 0 |
| Benzoyl Trialkyl Citrate (Example 2) | 0 | 0 | 67 | 0 |
| Pivaloyl Trialkyl Citrate (Example 3) | 0 | 0 | 0 | 67 |
| ESO | 3 | 3 | 3 | 3 |
| Therm-Chek LOHF 120 | 2 | 2 | 2 | 2 |

These plastisols were subjected to the test protocols listed above, with the results below:

| | A DINP | B Acetyl Trialkyl Citrate (Example 4) | C Benzoyl Trialkyl Citrate (Example 2) | D Pivaloyl Trialkyl Citrate (Example 3) |
|---|---|---|---|---|
| Brookfield Paste Viscosity at 20 RPM (cPs/Spindle No.) | | | | |
| Initial | 3,235/3 | 3,295/3 | 24,350/6 | 13,950/6 |
| 1 Day | 3,925/3 | 4,235/3 | 40,300/6 | 17,700/6 |
| 4 Day | 4,230/3 | 4,210/3 | 42,600/7 | 21,200/7 |
| 7 Day | 4,495/3 | 4,265/3 | 43,400/7 | 23,400/7 |
| 14 Day | 3,910/3 | 4,300/3 | 46,200/7 | 24,000/7 |
| 21 Day | 4,550/3 | 4,280/3 | 43,600/7 | 23,800/7 |
| 29 Day | 3,845/3 | 3,400/3 | 34,200/7 | 20,000/7 |
| Brookfield Paste Viscosity at 2 RPM (cPs/Spindle No.) | | | | |
| Initial | 3,200/3 | 3,450/3 | 33,000/6 | 50,000/6 |
| 1 Day | 3,700/3 | 4,300/3 | 54,500/6 | 51,000/6 |
| 4 Day | 3,800/3 | 4,700/3 | 58,000/7 | 56,000/7 |
| 7 Day | 3,950/3 | 5,050/3 | 62,000/7 | 62,000/7 |
| 14 Day | 3,900/3 | 5,100/3 | 68,000/7 | 74,000/7 |
| 21 Day | 4,150/3 | 5,150/3 | 62,000/7 | 66,000/7 |
| 29 Day | 3,850/3 | 3,400/3 | 40,000/7 | 54,000/7 |
| Raw Material Volatility (% loss) | | | | |
| RM Volatility | 1.61 | 8.79 | 2.73 | 8.81 |
| Gelation temperature (° C.) | | | | |
| Gelation temperature | 78 | 77 | 76 | 81 |
| Air Release (minutes) | | | | |
| Air Release | Good | Good | Poor | Poor |
| Hardness (Shore A) | | | | |
| Hardness | 83 | 83 | 90 | 88 |
| Heat Loss @ 180° F. (%) | | | | |
| 7 Days | 1.2 | 9.7 | 0.9 | 7.2 |
| 14 Days | 1.5 | 16.1 | 1.0 | 12.3 |
| Exudation @ 180° F. | | | | |
| After 1 week | None | None | None | Trace |
| After 2 weeks | None | Trace | None | Trace |
| After 3 weeks | None | Trace | None | Trace |
| After 4 weeks | None | Trace | None | Trace |

The viscosity characteristics of the plastisol made with acetyl trialkyl citrate were comparable to the viscosity characteristics of the plastisols made with the control DINP plasticizer. The viscosities of plastisols made with both benzoyl trialkyl citrate and pivaloyl trialkyl citrate were very high. The raw material volatility of plastisols made with both alkylated trialkyl citrates was higher than the control plastisols, but the plastisols made with benzoyl trialkyl citrate was only slightly higher than the DINP control. The gelation temperatures of all plastisols were comparable. Air release from the plastisol made with acetyl trialkyl citrate was comparable to the air release from the plastisols made with the control DINP plasticizer; air release from plastisols made with both benzoyl trialkyl citrate and pivaloyl trialkyl citrate was poor. The hardness values of the plastisol made with acetyl trialkyl citrate was identical to the hardness of the plastisols made with the control DINP plasticizer. Both the plastisols made with benzoyl trialkyl citrate and the plastisol made with pivaloyl trialkyl citrate were harder than the control plasticizer. The heat loss from plastisol made with benzoyl trialkyl citrate was very low, even less than the control, whereas significant heat loss took place from plastisols made with acetyl trialkyl citrate or pivaloyl trialkyl citrate. No exudation was detected in the control plastisol and the plastisol made with benzoyl trialkyl citrate, whereas plastisols made with acetyl trialkyl citrate or pivaloyl trialkyl citrate showed slight exudation. The Metrastat™ heat stability results of plastisols made with acetyl trialkyl citrate, benzoyl trialkyl citrate and pivaloyl trialkyl citrate as primary plasticizers were comparable to the Metrastat™ heat stability of the control plastisol made with DINP as the primary plasticizer.

EXAMPLES 12-15

Evaluation of Trialkyl Citrates and Acylated Trialkyl Citrates as Plasticizers for PVC Two citrate esters substantially free from esters in their hydroxyl portion (triisobutyl citrate and triisoamyl citrate) and the corresponding acetylated trialkyl citrates (acetylated triisobutyl citrate and acetylated triisoamyl citrate) from Example 6 were tested as primary plasticizers in PVC. A reference plastisol using DINP as primary plasticizer was tested as a control.

TABLE 12.1

Experimental Raw Material List: IC4 = triisobutyl citrate; A-IC4—acetylated triisobutyl citrate; IC5 = triisoamyl citrate; A-IC5 = acetylated triisoamyl citrate.

|  | DINP | IC4 | A-IC4 | IC5 | A-IC5 |
|---|---|---|---|---|---|
| Geon 121 AR | 100 | 100 | 100 | 100 | 100 |
| DINP | 67 | 0 | 0 | 0 | 0 |
| Triisobutyl citrate | 0 | 67 | 0 | 0 | 0 |
| Acetytated triisobutyl citrate | 0 | 0 | 67 | 0 | 0 |
| Triisoamyl citrate | 0 | 0 | 0 | 67 | 0 |
| Acetylated triisoamyl citrate | 0 | 0 | 0 | 0 | 67 |
| ESO | 3 | 3 | 3 | 3 | 3 |
| Therm-Chek 120 LOHF | 2 | 2 | 2 | 2 | 2 |

Plastisols made with trialkyl citrates and alkylated trialkyl citrates from Example 6 as primary plasticizer were subjected to the test protocols described above, with the results below:

|  | DINP | Tri-isobutyl citrate | Acetylated tri-isobutyl citrate | Tri-isoamyl citrate | Acetylated tri-isoamyl citrate |
|---|---|---|---|---|---|
| Brookfield Paste Viscosity at 20 RPM (cPs/Spindle No.) | | | | | |
| Initial | 2545/3 | 2840/3 | 6940/5 | 1680/3 | 1140/3 |
| 1 Day | 2695/3 | 3325/3 | 8040/5 | 2220/3 | 6800/5 |
| 3 Day | 3000/3 | 3435/3 | 7340/5 | 2505/3 | 6640/5 |
| 7 Day | 3000/3 | 3870/3 | 7040/5 | 2800/3 | 6820/5 |
| 30 Day | 3315/3 | 4780/3 | 5820/5 | 3345/3 | 6080/5 |
| Brookfield Paste Viscosity at 2 RPM (cPs/Spindle No.) | | | | | |
| 1 Day | 2450/3 | 2550/3 | 19600/5 | 1600/3 | 1100/3 |
| 3 Day | 2500/3 | 2950/3 | 23000/5 | 2100/3 | 6600/5 |
| 7 Day | 2750/3 | 3000/3 | 20400/5 | 2250/3 | 5000/5 |
| 30 Day | 2650/3 | 3350/3 | 17800/5 | 2700/3 | 5800/5 |
| Raw Material Volatility (% loss) | | | | | |
| RM Volatility | 1.74 | 18.61 | 5.72 | 7.77 | 12.76 |
| Gelation temperature (° C.) | | | | | |
| Gelation temperature | 72 | 65.5 | 77 | 71.5 | 74 |
| Hardness (Shore A) | | | | | |
| Hardness | 80 | 77 | 82 | 79 | 82 |
| Odor | Slight | Slight | Strong Acetic | Strong Banana | Slight Acetic |

The viscosity characteristics of plastisols from triisobutyl citrate and triisoamyl citrate were fairly comparable to the viscosity characteristics of control plastisol made with DINP, which increased about 25-30% over 30 days. The viscosity of plastisol made from acetylated triisobutyl citrate was much higher than the control from the beginning and increased, then decreased in viscosity over 30 days. The viscosity of the plastisol made from acetylated triisoamyl citrate as primary plasticizer was low in the initial reading, then increased substantially, followed by a decline at 30 days. The volatility (percent loss) values of the plastisols made with trialkyl citrates (triisobutyl citrate and triisoamyl citrate) and synthesized acylated trialkyl citrates (acetylated triisobutyl citrate and acetylated triisoamyl citrate) were greater than the volatility of the control plastisol. The gelation temperatures and hardness values of the control plastisol and the experimental plastisols were all roughly comparable. The odor of the control plastisol made with DINP was characteristically faint, as was the odor of the plastisol made from triisobutyl citrate. Acetylated triisobutyl citrate plastisol and the triisoamyl citrate plastisol had strong odors; the acetylated triisoamyl citrate plastisol had a slight odor. More rigorous cleanup procedures after formation of the acetylated triisobutyl citrate and acetylated triisoamyl citrate primary plasticizers may be required to eliminate the acetic acid odor. Plastisols made from triisobutyl citrate and triisoamyl citrate were darker in color than control, but the plastisols made from acetylated triisobutyl citrate and acetylated triisoamyl citrate primary plasticizers were as light as the control plasticizer. The Metrastat™ heat stability of plastisols made from triisobutyl citrate and triisoamyl citrate was poorer than the control plastisol; however, the plastisols made from acetylated triisobutyl citrate and acetylated triisoamyl citrate primary plasticizers was the same as the Metrastat™ heat stability of the plastisol made from control DINP plasticizer.

EXAMPLES 16 and 17

Evaluation of Acetylated Triisobutyl Citrates and Acetylated tri-2-ethylhexyl citrate as Plasticizers for PVC Acetylated triisobutyl citrate (from Example 1) and acetylated tri-2-ethylhexyl citrate from Example 7 were tested as primary plasticizers in PVC. A reference plastisol using DINP as primary plasticizer was tested as a control.

TABLE 16.1

Experimental Raw Material List

|  | DINP | Acetylated triisobutyl citrate | Acetylated tri-2-ethylhexyl citrate |
|---|---|---|---|
| Geon 121 AR | 100.0 | 100.0 | 100.0 |
| DINP | 67.0 | 0.0 | 0.0 |
| Acetylated triisobutyl citrate (Example 1) | 0.0 | 67.0 | 0.0 |
| Acetylated tri-2-ethylhexyl citrate (Example 7) | 0.0 | 0.0 | 67.0 |
| ESO | 3.0 | 3.0 | 3.0 |
| Therm-Chek 120 LOHF | 2.0 | 2.0 | 2.0 |

TABLE 16.2

Test results

|  | DINP | Acetylated triisobutyl citrate | Acetylated tri-2-ethylhexyl citrate |
|---|---|---|---|
| *Brookfield Paste Viscosity at 20 RPM (cPs). All results are with spindle 3* | | | |
| Initial | 2,260 | 1,735 | 4,390 |
| 1 Day | 2,485 | 2,065 | 4,480 |
| 4 Day | 2,895 | 2,390 | 4,760 |
| 7 Day | 2,905 | 2,445 | 4,425 |
| 14 Day | 2,980 | 2,485 | 3,890 |
| 21 Day | 3,060 | 2,570 | 4,015 |
| 28 Day | 3,070 | 2,580 | 4,155 |
| *Brookfield Paste Viscosity at 2 RPM (cPs). All results are with spindle 3* | | | |
| Initial | 1,800 | 1,450 | 3,550 |
| 1 Day | 2,050 | 1,900 | 4,200 |
| 4 Day | 2,700 | 2,150 | 4,450 |
| 7 Day | 2,700 | 2,400 | 4,400 |
| 14 Day | 2,850 | 2,450 | 3,850 |
| 21 Day | 2,950 | 2,550 | 4,000 |
| 28 Day | 2,950 | 2,550 | 4,050 |
| *Raw Material Volatility (% loss)* | | | |
| 1 gram held for 3 minutes at 400° F. | 2.0 | 9.3 | 7.3 |
| 1 gram, 3 minutes at Room Temp. | 0 | 0 | 5.4 |
| *Gelation temperature (° C.)* | | | |
| Gelation temperature | 73 | 68 | 76 |
| *Air Release* | | | |
| Air Release | Excellent | Excellent | Poor |
| *Hardness (Shore A)* | | | |
| Hardness | 80 | 79 | 89 |
| *Heat Loss @ 180° F. (%)* | | | |
| 7 Days | 0.6 | 7.8 | 0.9 |
| 14 Days | 0.7 | 14.0 | 0.8 |

TABLE 16.2-continued

Test results

| Exudation | DINP | | Acetylated triisobutyl citrate | | Acetylated tri-2-ethylhexyl citrate | |
|---|---|---|---|---|---|---|
| Exudation | 180° F. | RT | 180° F. | RT | 180° F. | RT |
| After 24 hours | None | None | None | None | None | None |
| After 1 week | None | None | None | None | Moderate | None |
| After 2 weeks | None | None | None | None | Heavy | None |
| After 3 weeks | None | None | None | None | Heavy | None |

The viscosity behavior of plastisol made with alkylated triisobutyl citrate in this case was very similar to the viscosity of the control plastisol and consistently somewhat lower. The viscosity behavior of plastisol made with alkylated tri-2-ethylhexyl citrate was slightly variable, with all values higher than the control plastisol throughout the test period. The raw material volatility (plasticizer volatility) of the control DINP plastisol was very low both at 400° F. and room temperature. The plasticizer volatility of the plastisol made from alkylated triisobutyl citrate was good at room temperature, but high at 400° F. The plasticizer volatility of plastisol made with alkylated tri(2-ethylhexyl) citrate was high under both test conditions. The gelation temperature of the plastisol made with acetylated triisobutyl citrate was desirable lower than the control plastisol; the gelation temperature of the alkylated tri(2-ethylhexyl) citrate plastisol was slightly higher than control but still within a workable range. The plastisol made with alkylated triisobutyl citrate showed excellent air release, similar to control. The air release from the plastisol made with alkylated tri(2-ethylhexyl) citrate, however, was poor. Similarly, the hardness values of the control plastisol and the alkylated triisobutyl citrate plastisol were very similar. The hardness value of the plastisol made with the alkylated tri(2-ethylhexyl) citrate was significantly higher. When tested for heat loss, the plastisol made with the alkylated tri(2-ethylhexyl) citrate showed very low heat loss, comparable to the control plastisol. The heat loss from plastisol made from alkylated triisobutyl citrate was substantially higher. No exudation was observed from the control plastisol made with DINP or the plastisol made with alkylated triisobutyl citrate, even after three weeks. The plastisol made from alkylated tri(2-ethylhexyl) citrate showed no exudation at room temperature but moderate and heavy exudation at 180° F. at the study period progressed. The Metrastat™ heat stabilities of the DINP plastisol and both acetylated trialkyl citrate plastisols were comparable.

EXAMPLE 18

Comparison of Acetylated tri-2-ethylhexyl citrate and Citrofol AH II as Plasticizers for PVC Acetylated tri-2-ethylhexyl citrate from Example 7 was tested as primary plasticizer in PVC and the properties compared to Citrofol™ AH II, a commercially available acetylated tri-2-ethylhexyl citrate (Junzbunzlauer, Boston, Mass.) as a plasticizer control.

TABLE 18.1

Experimental Raw Material List

|  | Citrofol ™ AH II | Acetylated tri-2-ethylhexyl citrate |
|---|---|---|
| Geon 121 AR | 100.0 | 100.0 |
| Citrofol ™ AH II (lot 471083406) | 67.0 | 0.0 |
| Acetylated tri-2-ethylhexyl citrate (lot 46910142) | 0.0 | 67.0 |
| Epoxidized soybean oil | 3.0 | 3.0 |
| Therm-Chek 120 LOHF | 2.0 | 2.0 |

TABLE 18.2

Plasticizer test results

|  | Citrofol ™ AH II | Acetylated tri-2-ethylhexyl citrate |
|---|---|---|
| Brookfield Paste Viscosity at 20 RPM (cPs/Spindle No.) | | |
| Initial | 9320/5 | 3720/4 |
| 1 Day | 11780/5 | 4530/4 |
| 4 Day | 11180/5 | 4570/4 |
| 7 Day | 9940/5 | 4550/4 |
| 14 Day | 9040/5 | 4560/4 |
| 21 Day | 8500/5 | 4390/4 |
| 28 Day | 8080/5 | 4130/4 |
| Brookfield Paste Viscosity at 2 RPM (cPs/Spindle No.) | | |
| Initial | 23800/5 | 3300/4 |
| 1 Day | 36600/5 | 3800/4 |
| 4 Day | 31400/5 | 4100/4 |
| 7 Day | 27400/5 | 4200/4 |
| 14 Day | 24000/5 | 4300/4 |
| 21 Day | 20600/5 | 3200/4 |
| 28 Day | 19200/5 | 2800/4 |
| Heat Loss (%) 1 week @ 180° F. | 0.2% | 0.8% |
| Heat Loss (%) 2 weeks @ 180° F. | −0.1% | 0.6% |
| Gelation temperature (° C.) | 80 | 76 |
| Air Release | Poor | Poor |
| Hardness (Shore A) | 90 | 89 |
| Plasticizer volatility (% loss) | 1.4% | 7.2% |

| | Citrofol ™ AH II | | Acetylated tri-2-ethylhexyl citrate | |
|---|---|---|---|---|
| Exudation | 180° F. | RT | 180° F. | RT |
| After 24 hours | None | None | None | None |
| After 1 week | None | None | Moderate | None |
| After 2 weeks | None | None | Heavy | None |
| After 3 weeks | None | None | Heavy | None |

The viscosity behavior of plastisol made with acetylated tri-2-ethylhexyl citrate was very consistent, and much lower than the viscosity of the control plastisol made with Citrofol™ AH II. The heat loss of plastisol made with acetylated tri-2-ethylhexyl citrate was acceptable but not comparable to the control plastisol, which exhibited very little heat loss. The plastisols had comparable gelation temperatures, air release, and Shore A hardness. The raw material volatility (plasticizer volatility) of the control DINP plastisol was low, and the plasticizer volatility of the plastisol made with acetylated tri-2-ethylhexyl citrate was high. Comparable Metrastat™ heat stability test times were obtained for films of both plastisols, with complete blackening of the strips taking place after about 40 minutes.

EXAMPLE 19

Evaluation of Acetylated tri-2-ethylhexyl citrate and Epoxidized acetyl-(2-ethylhexyl/3-hexenyl (10%)) citrate as Plasticizers for PVC.

Acetylated tri-2-ethylhexyl citrate from Example 7 and epoxidized acetyl-(2-ethylhexyl/3-hexenyl (10%)) citrate from Example 8 were tested as primary plasticizers in PVC. A reference plastisol using DINP as primary plasticizer was tested as a control in plastisols using ingredients listed in Table 19.1

TABLE 19.1

Experimental Raw Material List

|  | DINP | Acetylated tri-2-ethylhexyl citrate | Epoxidized acetyl-(2-ethylhexyl/3-hexenyl (10%)) citrate |
|---|---|---|---|
| Geon 121 AR | 100.0 | 100.0 | 100.0 |
| DINP | 67.0 | 0.0 | 0.0 |
| Acetylated tri-2-ethylhexyl citrate (Example 7) | 0.0 | 67.0 | 0.0 |
| Epoxidized acetyl-(2-ethylhexyl/3-hexenyl (10%)) citrate (Example 8) | 0.0 | 0.0 | 67.0 |
| ESO | 3.0 | 3.0 | 3.0 |
| Therm-Chek 120 LOHF | 2.0 | 2.0 | 2.0 |

TABLE 19.2

Test results

|  | DINP | Acetylated tri-2-ethylhexyl citrate | Epoxidized acetyl-(2-ethylhexyl/3-hexenyl (10%)) citrate |
|---|---|---|---|
| Brookfield Paste Viscosity at 20 RPM (cPs/Spindle No.) | | | |
| Initial | 2,370/3 | 6,540/4 | 4,340/3 |
| 1 Day | 2,670/3 | 9,140/4 | 4,370/4 |
| 3 Day | 3,095/3 | 9,540/4 | 4,430/4 |
| 7 Day | 3,395/3 | 9,600/5 | 4,480/4 |
| 15 Day | 3,405/3 | 9,960/5 | 4,550/4 |
| 21 Day | 3,355/3 | 9,940/5 | 4,530/4 |
| 28 Day | 3,575/3 | 11,080/5 | 4,660/4 |
| Brookfield Paste Viscosity at 2 RPM (cPs/Spindle No.) | | | |
| Initial | 1,900/3 | 3,200/4 | 3,250/3 |
| 1 Day | 2,350/3 | 10,900/4 | 3,300/4 |
| 4 Day | 2,750/3 | 11,500/4 | 3,700/4 |
| 7 Day | 3,050/3 | 12,000/5 | 3,400/4 |
| 15 Day | 3,200/3 | 8,600/5 | 3,400/4 |
| 21 Day | 3,200/3 | 7,400/5 | 3,400/4 |
| 28 Day | 3,400/3 | 5,800/5 | 3,500/4 |
| Plasticizer Volatility (% loss) | | | |
| 1 gram held for 3 minutes at 400° F. | 2.4% | 4.5% | 1.6% |
| 1 gram, 3 minutes at Room Temp. | 0.0% | 0.1% | 0.2% |
| Gelation temperature (° C.) | 72 | 77 | 76 |
| Air Release | Excellent | Good | Good |
| Hardness (Shore A) | 78 | 92 | 86 |
| Heat Loss @ 180° F. (%) | | | |
| 7 Days | 0.7% | 2.0% | 0.7% |
| 14 Days | 0.8% | 2.9% | 0.7% |

TABLE 19.2-continued

Test results

| Exuda-tion | DINP | | Acetylated tri-2-ethylhexyl citrate | | Epoxidized acetyl-(2-ethyl-hexyl/3-hexenyl (10%)) citrate | |
|---|---|---|---|---|---|---|
| | 180° F. | RT | 180° F. | RT | 180° F. | RT |
| 24 hours | None | None | Heavy | None | Moderate | None |
| 1 week | None | None | Heavy | None | Heavy | None |
| 2 weeks | None | None | Heavy | None | Heavy | None |
| 3 weeks | None | None | Heavy | Light | Heavy | None |
| 4 weeks | None | None | Heavy | Light | Heavy | None |
| 5 weeks | None | None | Heavy | Moderate | Heavy | None |

The initial viscosity values of the plastisols made with the control plasticizer were lower than the plastisols made with experimental plasticizers. The viscosity of the control plastisol increased for the first two weeks, then stabilized. The viscosity of the acetylated tri-2-ethylhexyl citrate plastisol was much higher than the control viscosity, and the viscosity at 2 rpm declined after the test at day 7. The viscosity of the epoxidized acetyl-(2-ethylhexyl/3-hexenyl (10%)) citrate plastisol was very stable, and hardly changed during the 28 days of testing.

The plasticizer volatility of acetylated tri-2-ethylhexyl citrate plastisol was somewhat high, but the volatility of the epoxidized acetyl-(2-ethylhexyl/3-hexenyl (10%)) citrate plastisol was very low. Comparable gelation temperatures were found for all three plastisols. The Air release properties of the experimental plastisols were good but did not match the excellent air release of the control plastisol. Higher hardness values were obtained with the experimental plasticizers. The heat loss values of the control plastisol and the epoxidized acetyl-(2-ethylhexyl/3-hexenyl (10%)) citrate plastisol were very low. Heat loss from the acetylated tri-2-ethylhexyl citrate plastisol was about three-fold greater than control. The Metrastat™ heat stability test times of both experimental plastisols were shorter that for the control plastisol. Plastisol made with acetylated tri-2-ethylhexyl citrate darkened more rapidly in this test than in Example 18. Heavy exudation at elevated temperature in the acetylated tri-2-ethylhexyl citrate plastisol and moderate exudation at elevated temperature in the epoxidized acetyl-(2-ethylhexyl/3-hexenyl (10%)) citrate plastisol was observed within 24 hours. Exudation subsequently did not take place in the control, but remained heavy for acetylated tri-2-ethylhexyl citrate at 180° F. and increased at room temperature. Exudation from epoxidized acetyl-(2-ethylhexyl/3-hexenyl (10%)) citrate plastisol became heavy at 180° F. but did not occur at room temperature.

What is claimed is:

1. A process for making an acylated trialkyl citrate ester or mixture of such esters, comprising a) forming a trialkyl citrate ester or esters by reacting citric acid, citric acid anhydride or citric acid chloride with one or more alcohols to substantial completion in the presence of a catalytically effective amount of a Lewis acid metal triflate catalyst while continually removing azeotropic water under reflux conditions, then b) in the same vessel and with the same Lewis acid metal triflate catalyst performing an acylation of the trialkyl citrate ester or esters by reaction with an acyl donor, and c) recovering at least a portion of the catalyst from the same vessel for reuse, wherein the process is performed without an intermediate step of isolating or purifying the trialkyl citrate ester or esters before the acylation thereof.

2. A process according to claim 1, wherein the process is carried out without addition of further catalyst for carrying out the acylation step.

3. A process of forming an epoxidized acylated trialkyl citrate ester or mixture of such esters, comprising producing the acylated trialkyl citrate ester or esters according to claim 2 and then epoxidizing the same.

4. The process according to claim 1, wherein catalyst is precipitated out and recovered by filtration.

5. The process according to claim 1, wherein catalyst is extracted into a water wash and recovered by removing water from the water wash containing the extracted catalyst.

6. The process according to claim 1, wherein the catalyst is supplied for the process in a solid form and is recovered by filtration.

* * * * *